United States Patent [19]

Dellacoletta et al.

[11] Patent Number: 5,359,084
[45] Date of Patent: Oct. 25, 1994

[54] METHOD OF PREPARING AROMATIC ETHER BISIMIDES

[75] Inventors: Brent Dellacoletta, Evansville; Roy R. Odle, Mt. Vernon, both of Ind.

[73] Assignee: General Electric Company, Pittsfield, Mass.

[21] Appl. No.: 18,993

[22] Filed: Feb. 18, 1993

[51] Int. Cl.$^5$ .......................................... C07D 403/12
[52] U.S. Cl. .................................. 548/461; 548/476; 548/480; 548/481
[58] Field of Search ............... 548/461, 476, 480, 481

[56] References Cited

U.S. PATENT DOCUMENTS

| | | | |
|---|---|---|---|
| 3,852,242 | 12/1974 | White | 260/47 |
| 3,879,428 | 4/1975 | Heath et al. | 206/346.3 |
| 3,992,407 | 11/1976 | Markezich | 206/326 N |
| 4,017,511 | 4/1977 | Williams, III | 260/326 N |
| 4,048,190 | 9/1977 | Johnson et al. | 260/326 N |
| 4,054,577 | 10/1977 | Relles et al. | 252/511 X |
| 4,202,993 | 5/1980 | Takekoshi | 568/723 |
| 4,247,464 | 1/1981 | Relles et al. | 568/723 X |
| 4,257,953 | 3/1981 | Williams, III et al. | 568/723 X |
| 4,273,712 | 6/1981 | Williams, III et al. | 260/326 N |
| 4,520,204 | 5/1985 | Evans | 548/461 |
| 4,950,727 | 8/1990 | Guggenheim et al. | 528/26 |
| 5,032,451 | 7/1991 | Corley | 428/289 |

FOREIGN PATENT DOCUMENTS

| | | |
|---|---|---|
| 0119576 | 9/1984 | European Pat. Off. . |
| 0141692 | 5/1985 | European Pat. Off. . |
| 0273159 | 7/1988 | European Pat. Off. . |
| 254303 | 2/1988 | U.S.S.R. . |

*Primary Examiner*—Patricia L. Morris
*Assistant Examiner*—Jacqueline Haley

[57] ABSTRACT

A method for preparing an aromatic ether bisimide is provided. The mixture obtained from reacting a substituted phthalimide with a metal salt of a hydroxy aromatic compound in a non-polar solvent is extracted with about 4% to about 6% by weight aqueous alkali hydroxide solution to remove the reaction's by-products and thus provide substantially pure aromatic ether bisimide. The method is particularly suitable for extracting aromatic ether bisimide by-products from a continuous process preparing aromatic ether bisimide.

25 Claims, No Drawings

METHOD OF PREPARING AROMATIC ETHER BISIMIDES

BACKGROUND

1. Field of the Invention

The present invention relates to improved extractions which provide better removal of extraneous materials or by-products produced while preparing aromatic ether bisimides and thus increasing the yield of the desired bisimide product. The invention also relates to extractions of by-products from continuous processes of preparing aromatic ether bisimides.

2. Background Art

Aromatic ether bisimides are useful as chemical intermediates in the production of a number of important compounds. For example, 2,2-bis[4-(N-methylphthalimide-4-oxyphenyl]propane (hereinafter "bisphenol A-bisimide" or "BPA-BI") is used in the preparation of polyetherimides which are commercially important thermoplastics. In certain processes aromatic ether bisimides are prepared from an alkali metal salt of a hydroxyaromatic compound which undergoes a nucleophilic displacement reaction with a substituted phthalimide. See, for example, U.S. Pat. No. 4,520,204. The displacement reaction is usually effected in a relatively non-polar organic diluent such as benzene, toluene, xylene, chlorobenzene, tetrahydrofuran, octane, acetonitrile or the like in the presence of a phase transfer catalyst, typically a tetraalkylammonium salt. See, for example, U.S. Pat. Nos. 4,257,953; 4,273,712; and 4,247,464. A frequently used diluent for this reaction is toluene.

The reaction mixture containing the prepared aromatic ether imide typically contains extraneous material or by-products, such as unreacted substituted phthalimide, phase transfer catalyst and various inorganic salts formed in the displacement reaction. Such by-products, unless removed, tend to compromise the properties of the end products which are subsequently prepared from the bisimides.

As indicated above, bisimides can be used to prepare polyetherimides. Specifically, BPA-BI is hydrolyzed to a tetraacid derivative and dehydrated to form BPA-dianhydride. BPA-dianhydride ("BPA-DA") is reacted with organic diamines (for example metaphenylene diamine) to make the desired polyetherimide. Synthesis of a suitable bisimide and its conversion to a dianhydride is more specifically disclosed and claimed in U.S. Pat. No. 3,879,428.

The thermal stability and other properties of polyetherimide resins are very much dependent on the purity of the BPA-DA used in their synthesis. It has been found that the amount of impurities in BPA-DA derived from BPA-BI often is greater than desirable. Such impurities typically include bisphenol-A, 4-nitrophthalimide and 4-bisphenol-A-monoimide. These by-products in the past were separated by extraction with aqueous and/or dilute aqueous alkali. See U.S. Pat. No. 4,520,204 to Evans. For example, extractions with dilute (1%) alkali hydroxide solutions heated to about 70°-80° C. have been satisfactorily employed in certain instances. See U.S. Pat. No. 4,247,464 to Relles et al. In fact, aqueous solutions of 1% by weight alkali hydroxide have been frequently relied upon to extract by-products from the precursors to numerous commercial polyetherimides. Processes employing 1% alkali metal hydroxide extraction solutions typically comprise multiple extraction steps in order to completely remove impurities from the reaction mixture, especially to completely remove the monoimide impurities which due to the fact that it has a solubility similar to the bisimide product is not easily removed from the organic phase. These multiple step processes, however, can be time consuming, create a large volume of aqueous waste and incur high disposal costs. The waste is usually incinerated and the energy consumption necessary to drive off the aqueous portion of the waste is high. Moreover, hydrolysis of bisimide occurs at each extraction, thereby reducing the yield of bisimide. Physical losses of bisimide are also incurred at each extraction/separation step.

The costs and disposal concerns of the current methods of extracting aromatic ether bisimide by-products has thus far made it difficult to efficiently prepare these bisimides. A continuous process would be desirable over a "batch" process for several reasons, one of which is efficiency that can be gained when preparing large volumes of bisimide. Typically, continuous processes also provide for a more consistent process and product.

Accordingly, there remains a need and desire for improved processes-for removing by-products and impurities created during the production of aromatic ether bisimides. Faster removal of impurities, the reduction of aqueous volume extract, and the alleviation of disposal problems, concentration and incineration costs incurred by current procedures are also desirable. These issues are addressed by the present invention.

It would also be preferable to reduce the hydrolysis of the desired bisimide and bisimide yield loss which occurs with the current extraction processes, as well as reduce the physical losses of bisimide that are incurred with each multiple/extraction step. Both of these, too, are objects of the present invention.

Moreover, an extraction process which goes towards meeting these goals can be used to improve a continuous process of preparing aromatic ether bisimides, with the improvement thereof also a goal of this invention.

SUMMARY OF THE INVENTION

The foregoing issues in the production of aromatic ether bisimides are satisfactorily addressed by the present invention.

The invention comprises removing by-products from a reaction mixture obtained from the reaction of a substituted phthalimide with an alkali metal salt of a hydroxy aromatic compound in a non-polar organic solvent under imide-forming conditions, comprising extracting the by-products with an aqueous solution of about 4% to about 6% by weight alkali.

The above method can also be used to provide a new continuous method for preparing aromatic ether bisimides. The new continuous method comprises:
  (a) providing at least one substituted phthalimide and at least one alkali metal salt of a hydroxy aromatic compound,
  (b) reacting the substituted phthalimide with the alkali metal salt of the hydroxy aromatic compound in a non-polar organic solvent thereby providing an aromatic ether bisimide and by-products thereof, and
  (c) extracting the by-products of the reaction in (b) with an aqueous solution of about 4% to about 6% by weight alkali.

By extracting by-products with an alkali solution of about 4 to 6%, a substantially pure aromatic ether bisimide can be prepared without resort to lengthy extraction periods. In addition, this method generally results in a more complete removal of impurities than previously has been attained with 1% alkali solutions. Further, and quite unexpectedly, hydrolysis of the desired aromatic ether bisimide is minimized. For instance, conventional extraction methods typically avoid extracting with alkali hydroxide concentrations higher than 1% because of increased hydrolysis of the desired bisimide product. However, it has been found that by extracting with about 4% to 6% alkali aqueous solution in short periods of time, e.g., in about thirty seconds to about one minute, the impurities are totally removed with minimal hydrolysis. It also has been found that extraction volume can be reduced, thus reducing the disposal, concentration and incineration costs incurred. Yields of bisimide are increased when using a 4% to 6% by weight alkali solution because extraction can typically be performed in no more than two steps, and usually in only one step. In addition, the shorter extraction times and smaller extraction volumes also make the method of this invention suitable for extracting by-products from the product mixture of a continuous process of preparing aromatic ether bisimides. The shorter extraction times make for a more efficient process and the smaller extraction volumes reduce disposal costs of the aqueous wastes that are produced during a continuous process. The higher alkali concentrations also insure a more complete extraction.

DETAILED DESCRIPTION OF THE INVENTION

The general reaction which occurs when employing this invention is the nucleophilic displacement reaction of at least one substituted phthalimide with at least one alkali metal salt of a hydroxyaromatic compound. Suitable substituted phthalimides are illustrated by the formula

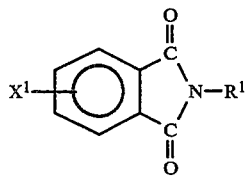

wherein $R^1$ is hydrogen, an alkyl radical having from 1 to 8 carbon atoms or an aryl radical having from 6 to 13 carbon atoms and $X^1$ is a nitro or halo radical, i.e., fluoro, chloro, bromo, or iodo and preferably chloro or bromo. Preferably, $R^1$ is a $C_1$-$C_4$ alkyl, such as methyl, and $X^1$ is nitro.

Specific suitable substituted phthalimides include, but are not limited to, 4-nitro-N-phenylphthalimide; 3-nitro-N-phenylphthalimide; 4-nitro-N-methylphthalimide; 3-nitro-N-methylphthalimide; 4-fluoro-N-methylphthalimide; 3-fluoro-N-methylphthalimide; 4-chloro-N-methylphthalimide; 3-chloro-N-methylphthalimide, etc. These substituted phthalimides can be made by standard procedures, such as effecting reaction between substantially equal mols of the corresponding phthalic anhydride and an organic amine in the presence of refluxing acetic acid. Suitable organic amines include, but are not limited to, aniline, toluidine, etc., methylamine, ethylamine, etc.

The salt which undergoes a nucleophilic displacement reaction with the substituted phthalimide is an alkali metal, e.g., lithium, sodium, or potassium (preferably sodium) salt of at least one hydroxyaromatic compound.

Suitable hydroxyaromatic compounds are those having the formula $Q(OH)_n$, wherein Q is a monovalent or divalent aromatic-based radical and n is 1 or 2. Such radicals include those in groups (1)–(3) below.

(1) Hydrocarbon radicals such as aromatic and mixed aliphatic-aromatic and alicyclic-aromatic radicals are suitable. Such radicals are known to those skilled in the art and include, but are not limited to, phenyl, tolyl, xylyl, phenylene, tolylene, xylylene, 1,4-napthylene, 1-5-napthylene, p,p'-biphenylene and 2,2-(p,p'-diphenylene)propane (all isomers being included).

(2) Substituted hydrocarbon radicals such as radicals containing non-hydrocarbon substituents which do not alter the predominantly hydrocarbon character of the radical are suitable. Such substituents include, but are not limited to, halo, alkoxy (especially lower alkoxy), carbalkoxy and alkyl sulfone.

(3) Hetero radicals such as radicals which, while predominantly hydrocarbon in character, contain atoms other than carbon present in a chain or ring are suitable. Such hetero atoms will be apparent to those skilled in the art and include, but are not limited to, nitrogen, oxygen and sulfur. For the most part, not more than three substituents or hetero atoms will be present for each 10 carbon atoms in the hydrocarbon-based radical.

The radical Q is most often a divalent radical derived from benzene or a substituted benzene, biphenyl or a substituted biphenyl, or a diphenylalkane which may contain substituents on one or both aromatic radicals. The following specific radicals are preferred as Q:

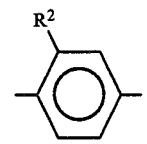

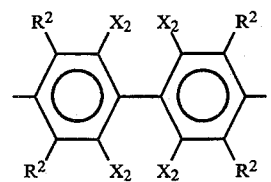

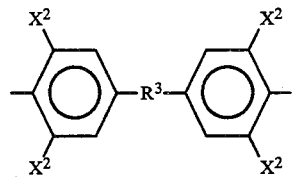

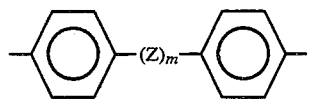

wherein each $R^2$ is independently hydrogen or methyl, $R^3$ is a straight-chain or branched alkylene radical containing 1–5 carbon atoms and is most often the isopropylidene radical, and each $X^2$ is independently hydrogen or halogen, e.g., usually chlorine or bromine. Z is a member selected from the class consisting of divalent radicals of the formulas

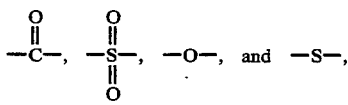

where m is 0 or 1. Mixtures of the foregoing formulas are also contemplated.

The alkali metal salts of the hydroxy aromatic compound can be made by various procedures, including the flash evaporation of bisphenoxide alkali metal salt hydrate or an aqueous slurry thereof, as shown by U.S. Pat. No. 4,202,993 of Tohru Takekoshi, or by azeotroping water from an aqueous mixture of bisphenoxide alkali metal salt and toluene. Additional procedures are shown in U.S. Pat. No. 3,852,242 to White.

Specific alkali metal salts of the above-described hydroxy aromatic compounds are sodium and potassium salts of phenols, such as phenol, cresol, naphthol, etc. Dihydric phenols include but are not limited to:

2,2-bis(2-hydroxyphenyl)propane;
2,4'-dihydroxydiphenylmethane;
bis(2-hydroxyphenyl)methane;
2,2-bis-(4-hydroxyphenyl)propane often identified as "bisphenol-A" or "BPA";
1,1-bis-(4-hydroxyphenyl)ethane;
1,1-bis-(4-hydroxyphenyl)propane;
2,2-bis-(4-hydroxyphenyl)pentane;
3,3-bis-(4-hydroxyphenyl)pentane;
4,4'-dihydroxybiphenyl;
4,4'-dihydroxy-3,3,5,5'-tetramethylbiphenyl;
2,4'-dihydroxybenzophenone;
4,4'-dihydroxydiphenylsulfone;
2,4'-dihydroxydiphenylsulfone;
4,4'-dihydroxydiphenylsulfoxide;
4,4'-dihydroxydiphenylsulfide;
hydroquinone;
resorcinol;
3,4-dihydroxydiphenylmethane;
4,4'-dihydroxybenzophenone; and
4,4'-dihydroxydiphenylether.

Reaction is effected between the substituted phthalimide and the salt of the hydroxy aromatic compound, e.g., a phenoxide salt, to prepare the desired bisimide. Phenoxide salt signifies a salt in the presence of a nonpolar solvent and an effective amount of a phase transfer catalyst. The reaction is followed by the recovery of the resulting aromatic bis(ether phthalimide). It is preferred to effect the reaction under substantially anhydrous conditions, although small amounts of moisture can be tolerated.

Temperatures at which reaction between a phenoxide salt and a substituted phthalimide can be effected are in the range of about 25° C. to about 180° C., and preferably lie between about 100° and about 120° C. Suitable proportions of reactants are in the range of about 5 to about 150% by weight based on solvent. A suitable ratio of equivalents of phase transfer catalyst to phenoxide salt is in the range of about 0.005 to about 2. Equivalent amounts of the phenoxide salts and substituted phthalimide can be used, while higher or lower amounts of either will not substantially interfere with the formation of the desired ether phthalimide. In preparing aromatic bisether phthalimides, however, two mols of the substituted phthalimide per mol bisphenoxide salt is preferred.

Any nonpolar organic solvent which does not react with the reactants during the formation of the ether phthalimide can be used in the reaction. Suitable nonpolar organic solvents include, but are not limited to, toluene, benzene, chlorobenzene, o-dichlorobenzene, 1,2,4-trichlorobenzene, xylene, tetrahydrofuran, acetonitrile, octane, etc. Toluene is the preferred solvent for the preparation of BPA-BI.

Various classes of compounds may be used as phase transfer catalysts in the method of this invention. These include, but are not limited to, quaternary ammonium and phosphonium compounds and crown ethers. Illustrative phase transfer catalysts are tetraethylammonium bromide, tetraethylammonium acetate, tetrabutylammonium bromide, tetraphenylphosphonium bromide and 18-crown-6 (1,4,7,10,13,16-hexaoxacyclooctadecane). Mixtures of catalysts can also be used. The particularly preferred phase transfer catalysts are tetraalkylammonium halides, tetraarylphosphonium halides and crown ethers. Most preferred is bis-tetralkylammonium bromide. See U.S. Pat. No. 4,273,712.

As indicated above, by-products are produced during the reaction of the substituted phthalimide and hydroxyaromatic compound salt. Typical by-products include:

(1) reaction solids including aromatic ether monoimides of the formula,

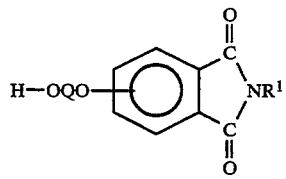

(2) alkali metal substituted phthalic salts of the formula,

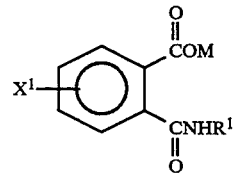

(3) unreacted substituted N-alkyl phthalimide of the formula,

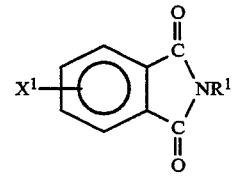

and (4) alkali metal aromatic hydrocarbon salts of the formula,

Also included in the reaction mixture are alkali metal nitro or halo salts and substituted phthalic acid amides of the formula,

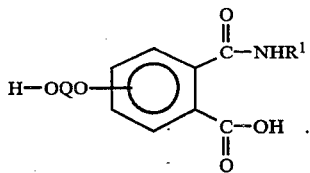

Q, $R^1$, $X^1$ and m are defined earlier. M can include alkali metal ions, for example, sodium, potassium, etc.

Typical by-products present in the reaction mixture following the preparation of BPA-BI include the starting materials, e.g., 4-nitro-N-methyl phthalimide ("4-NPI"), the salt of BPA, BPA-monoimide and various salt derivatives (such as sodium nitrite) produced when the nitro group is displaced in the formation of the bisimide. The by-products will also comprise the phase transfer catalyst.

The by-products of the above reaction are removed according to the invention by extracting the non-polar solvent based reaction mixture with an alkali aqueous solution of about 4% to about 6%, and preferably about 5%. By using such alkali solutions, small volumes can be used to completely extract by-products quite rapidly, i.e., in less than thirty seconds. A "complete extraction" or a "substantially complete extraction" as used herein means that no more than about 0.1% by weight impurities remain after the extraction step. Complete, i.e., 100%, removal can, however, typically be expected when using the method of this invention under the preferred conditions.

The optimum percentage of alkali in solution, however, depends on the equipment employed to perform the extraction, the variability of impurities in the bisimide batch being extracted, as well as the residence time. Reaction mixtures having high levels of impurities typically require extractions with solutions having a higher level of alkali or higher ratios of aqueous solution to solvent. Certain impurities, such as sodium nitrite, can also affect the percentage of alkali employed. Reaction mixtures having a high level of by-product/impurities such as sodium nitrite usually require extractions with solutions having lower levels of alkali, or higher ratios of aqueous alkali solution to solvent. In addition, the geometry of certain reactors provide for slow phase separating, thus dictating a large residence time. In those instances, the alkali level or strength should be reduced.

For a continuous process of preparing bisimides, and the impurities expected therefrom, a preferable alkali percentage, by weight, is 5%. Extraction residence times of about 30 seconds to one minute can be expected using such solutions. The results below indicate that extractions under those conditions can be expected to completely remove the impurities created by such a continuous reaction, and do so with minimal hydrolysis. The method of this invention can be typically performed with no more than about 3% hydrolysis by weight. Such results are completely unexpected from those previously obtained using 1% alkali solutions for extraction. As indicated earlier, 1% alkali solutions require multiple washes which in turn decrease yield through hydrolysis that occurred at each wash step. These extractions also required lengthy residence times which also led to increased hydrolysis. Moreover, the increased residence times made such extraction solutions impractical for continuous processes.

The alkali aqueous solution can comprise solution recycled from any aqueous wash solutions used on the reaction product mixture. Alkali solution spent in previous extractions also may be recycled for later extractions. The recycled solutions are collected using conventional techniques, adjusted to the suitable alkali concentration and then employed when needed.

Suitable alkali solution to solvent ratios are in the range of about 8:50 to about 20:50, with a range of about 9:50 to about 11:50 preferred. Solutions having higher concentrations of alkali can be effectively used at lower ratios. Lower ratios could also be used if the reaction mixture is prefiltered prior to performing the extraction step. An alkali solution to solvent ratio of about 1:30 would be suitable in those instances. The above ratios are suitable for typical reaction mixtures which comprise 20 to 25% product and impurities. In general, higher ratios will be required for reaction mixtures comprising higher percentages of product and impurities.

As mentioned above, however, the present invention typically reduces the volume of aqueous solution required for the extraction. A two to three fold reduction can be expected over the prior art processes which employ 1% by weight alkali and two or three extraction steps.

The residence time for the extraction can be between 1 second and four minutes, depending on the amount of alkali in the extraction solution. Shorter times of about 5 to thirty seconds to one minute, however, are typically sufficient for the 5% alkali solutions which are employed at the preferred alkali solution to solvent ratio mentioned above. As mentioned above, the shorter times are preferred because longer residence times usually result in the hydrolysis of the bisimide, thereby reducing yield. Shorter residence times are also typically required for the more alkaline solutions in order to avoid hydrolysis.

The extraction is typically carried out at a temperature of about 75° to 80° C., with about 80° C. preferred. Vigorous agitation during the extraction is also preferable.

Suitable alkali solutions can be prepared from alkali metal hydroxides such as sodium and potassium hydroxide, as well as from other strong alkali solutions such as potassium carbonate, sodium carbonate, and sodium phosphate. Ammonium hydroxide may also be used.

After the extraction, any solvent that is present is stripped to yield the desired bisimide product. Yields are generally in the range of 80 to 98%, and under typical conditions are 90 to 96%.

The effectiveness of this method was quite unexpected. For instance, a one step extraction using five times more than the typical amount of aqueous 1% sodium hydroxide only removed a fraction of the monoimide by-product in the time the 5% solution removed substantially all of the by-product. Further, the level of the monoimide was higher than that obtained using 5% sodium hydroxide.

The following examples are provided as illustrative of the invention described above and should not be interpreted as limiting the scope of the claims appended hereto.

EXAMPLES

The extractions below were performed on displacement mixtures from the reaction of 4-nitro-N-methylphthalimide and bisphenol-A in toluene. The reaction was carried out under conventional conditions illustrated in U.S. Pat. No. 4,273,712.

The displacement mixtures from the batches tested herein comprised the following amounts of bisphenol-A monoimide (MI), bisphenol-A (BPA), 4-nitro-phthalimide (4NPI) and hydrolyzed bisphenol-A bisimide (HYBI) by-products or impurities (% by weight of total displacement mixture):

| BATCH | MI | BPA | 4NPI | % HYBI |
|---|---|---|---|---|
| 1 | 1.13 | 3.20 | 1.24 | 1.26 |
| 2 | 1.43 | 2.05 | 0.33 | 0.79 |
| 3 | 1.04 | 4.97 | 0.12 | 1.35 |
| 4 | 1.06 | 1.25 | 1.31 | 1.10 |

Samples of the displacement mixtures were extracted at 80° C. with vigorous agitation. Single step extractions, except as otherwise noted, were performed at various residence times in seconds (TIME) and various sodium hydroxide concentrations (% NaOH). The results are indicated in Table 1 below.

TABLE 1
THE EFFECT OF ALKALI %

| BATCH | TIME | % NaOH | RATIO | % HYBI | MI | BPA | 4NPI |
|---|---|---|---|---|---|---|---|
| 1 | 5 | 1 | 10/53 | 1.05 | 1.14 | 0 | 0.81 |
| 1 | 5 | 2 | 10/53 | 1.19 | 0.97 | 0 | 0.87 |
| 1 | 5 | 5 | 10/53 | 1.26 | 0 | 0 | 0 |
| 1 | 30 | 1 | 10/53 | 1.19 | 0.95 | 0.99 | 0.95 |
| 1 | 30 | 2 | 10/53 | 1.28 | 0.74 | 0 | 0.42 |
| 1 | 30 | 5 | 10/53 | 1.37 | 0 | 0 | 0 |
| 1 | 240 | 1 | 10/53 | 1.18 | 0.66 | 0.10 | 0 |
| 1 | 240 | 2 | 10/53 | 1.38 | 0.11 | 0 | 0 |
| 1 | 240 | 5 | 10/53 | 2.13 | 0 | 0.46 | 0 |
| 3 | 5 | 5 | 10/53 | * | * | * | * |
| 3 | 5 | 2 | 13/53 | 2.07 | 0.68 | 0.04 | 0 |
| 3 | 5 | 3 | 13/53 | 1.97 | 0.21 | 0.16 | 0 |
| 3 | 5 | 4 | 13/53 | 2.22 | 0.02 | 0.20 | 0 |
| 3 | 5 | 5 | 13/53 | 2.35 | 0 | 0.02 | 0 |
| 3 | 5 | 6 | 13/53 | 2.34 | 0 | 0.05 | 0 |
| 4 | 60 | 1 | 10/53 | 1.56 | 0.37 | 0.44 | 0 |
| 4 | 60 | 4 | 10/53 | 0.66 | 0.89 | 0.13 | 0.15** |
| 4 | 60 | 5 | 10/53 | 1.40 | 0 | 0 | 0 |
| 4 | 60 | 6 | 10/53 | 1.50 | 0 | 0.02 | 0 |
| 4 | 60 | 7 | 10/53 | *** | *** | *** | *** |

*A heterogeneous mixture of impurities was present, i.e., the extraction did not occur or was not complete. Illustrates that with batches having high levels of impurities, larger volumes of alkali aqueous solutions are required for the shorter extraction times. Compare this extraction with a similar extraction of Batch #1.
**Experimental error is quite likely, especially when results are viewed in light of the 4% NaOH extraction for Batch 3, the where hydrolysis level is low. In comparison with extractions on Batch 3, the Batch 4 extraction should be higher in view of the Batch 4 extraction being longer. The lower RATIO in the Batch 4 extraction should not account for that large a decrease in hydrolysis.
***A heterogeneous mixture of impurities was present, i.e., the extraction did not occur or was not complete. In this instance, the alkali level was too high for the given volume of aqueous solution and this is believed to have caused the mixture to be heterogenous.

The above results indicate that a 5% alkali metal solution at an alkali solution to solvent ratio of about 10/53 completely removes all of the impurities in as little as five seconds and with minimized hydrolysis of bisimide product. This ratio falls within the preferred ratio of about 9:50 to about 11:50. The four minute extraction with 5% NaOH solution illustrates the maximum time a suitable extraction may be made with a 10/53 ratio of aqueous solution to solvent. It is believed that after four minutes enough BPA-BI had hydrolyzed to begin protonating the BPA. The protonated BPA then began going back into the organic phase. As indicated above, about 0.46 by weight BPA was present.

The one step extractions with 1% and 2% alkali metal failed to completely remove MI and more washes would thus be needed to completely remove the MI.

The results also indicate that at a RATIO of 13/53 and residence time of five seconds a suitable extraction can be obtained at a range of about 4% to about 6% by weight alkali metal. At 4% alkali, complete extraction of MI and substantially complete extraction of the other impurities was achieved. Complete removal of impurities is also achieved at 6% by weight alkali with only slightly elevated HYBI. As mentioned above, the elevated HYBI probably accounts for the presence of BPA after the extraction, especially for the extractions having longer residence times. The increased hydrolysis in this instance resulted from the higher alkali concentration.

TABLE 2
THE EFFECT OF RESIDENCE TIME

| BATCH | TIME | % NaOH | RATIO | % HYBI | MI | BPA | 4NPI |
|---|---|---|---|---|---|---|---|
| 1 | 5 | 1 | 10/53 | 1.05 | 1.14 | 0 | 0.81 |
| 1 | 30 | 1 | 10/53 | 0.95 | 0.95 | 0.09 | 0.95 |
| 1 | 240 | 1 | 10/53 | 0.66 | 0.66 | 0.10 | 0 |
| 1 | 5 | 2 | 10/53 | 1.19 | 0.07 | 0 | 0.87 |
| 1 | 30 | 2 | 10/53 | 0.74 | 0.74 | 0 | 0.42 |
| 1 | 240 | 2 | 10/53 | 0.11 | 0.11 | 0 | 0 |
| 1 | 5 | 5 | 10/53 | 1.26 | 0 | 0 | 0 |
| 1 | 15 | 5 | 10/53 | 1.36 | 0 | 0 | 0 |
| 1 | 30 | 5 | 10/53 | 1.37 | 0 | 0 | 0 |
| 1 | 60 | 5 | 10/53 | 1.71 | 0 | 0 | 0 |
| 1 | 120 | 5 | 10/53 | 1.84 | 0 | 0 | 0 |
| 1 | 240 | 5 | 10/53 | 2.13 | 0 | 0 | 0 |
| 2 | 5 | 5 | 10/53 | 0.79 | 0 | 0 | 0 |
| 2 | 15 | 5 | 10/53 | 0.80 | 0 | 0 | 0 |
| 2 | 30 | 5 | 10/53 | 0.88 | 0 | 0 | 0 |
| 2 | 60 | 5 | 10/53 | 1.21 | 0 | 0 | 0 |
| 2 | 120 | 5 | 10/53 | 1.91 | 0 | 0 | 0 |
| 2 | 240 | 5 | 10/53 | 1.27 | 0 | 0 | 0 |
| 3 | 5 | 5 | 13/53 | 2.35 | 0 | 0.02 | 0 |
| 4 | 5 | 5 | 10/53 | 1.10 | 0 | 0.03 | 0 |
| 4 | 60 | 5 | 10/53 | 1.39 | 0 | 0 | 0 |
| 4 | 120 | 5 | 10/53 | 1.56 | 0 | 0.03 | 0 |
| 4 | 240 | 5 | 10/53 | 1.96 | 0 | 0.02 | 0 |

The above results primarily show that 5% NaOH alkali solutions employed at 10:53 RATIO's can satisfactorily remove impurities from the displacement reactions over a range of residence times. The above results also confirm that as little as five seconds are needed for a 5% NaOH at a 10/53 RATIO to completely extract all of the impurities present. The results also show that even at longer residence times, e.g., four minutes, the 1% and 2% NaOH extractions failed to completely remove all of the impurities of Batch #1.

TABLE 3
THE EFFECT OF AQUEOUS VOLUME TO SOLVENT VOLUME RATIO

| BATCH | TIME | % NaOH | RATIO | % HYBI | YI | MI | BPA | 4NPI |
|---|---|---|---|---|---|---|---|---|
| 1 | 30 | 5 | 7/53 | HETEROGENEOUS | | | | |
| 1 | 30 | 5 | 8/53 | 1.44 | | 0 | 0 | 0 |
| 1 | 30 | 5 | 9/53 | 1.46 | | 0 | 0 | 0 |
| 1 | 30 | 5 | 10/53 | 1.37 | | 0 | 0 | 0 |
| 4 | 60 | 5 | 10/53 | 1.39 | 20 | 0 | 0 | 0 |
| 4 | 60 | 5 | 15/53 | 1.49 | 18 | 0 | 0.02 | 0 |

TABLE 3-continued

THE EFFECT OF AQUEOUS VOLUME TO SOLVENT VOLUME RATIO

| BATCH | TIME | % NaOH | RATIO | % HYBI | YI | MI | BPA | 4NPI |
|---|---|---|---|---|---|---|---|---|
| 4 | 60 | 5 | 20/53 | 1.46 | 19 | 0 | 0 | 0 |

The above results show that at the preferred NaOH %, the RATIO has little effect on removing impurities. There is, however, a critical volume at which a sufficient volume of alkali is necessary to keep the materials in solution, e.g., more than 7/53 is required for 5% solutions, because at that ratio a heterogeneous mixture of impurities and by-products occurred.

Multiple Washing

The last parameter that was studied was the effect of multiple washes (Table 4). This study was run primarily to see the effect on hydrolysis and would be a "best case" plant model. The first washes in this series with 1% by weight NaOH typically gave a large "rag layer" that took about 5 minutes to settle. However, the 5% by weight NaOH phase separated very quickly (about 30 seconds).

TABLE 4

| BATCH | WASH | TIME | % NaOH | RATIO | % HYBI |
|---|---|---|---|---|---|
| 3 | 1 | 60 | 5 | 10/53 | 2.04 |
| 3 | 2 | 60 | 5 | 10/53 | 0.09 |
| 3 | 3 | 60 | 5 | 10/53 | 0.05 |
| TOTAL VOLUME HYBI BY WEIGHT = 2.18 | | | | | |
| 4 | 1 | 60 | 1 | 10/53 | 1.56 |
| 4 | 2 | 60 | 1 | 10/53 | 0.11 |
| 4 | 3 | 60 | 1 | 10/53 | 0.02 |
| TOTAL HYBI BY WEIGHT = 1.69 | | | | | |
| 4 | 1 | 5/90* | 5 | 10/53 | 1.40 |
| 4 | 2 | 5 | 5 | 10/53 | 0.10 |
| TOTAL HYBI BY WEIGHT = 1.50 | | | | | |

*First wash - 5 second agitation with 90 minute standing time

Extraction Efficiency

A mixture of bisphenol A monoimide (MI) (0.10 g, 0.258 mmoles) and bisphenol A bisimide (BI) (4.9 g, 9.0 moles) is dissolved in 25 ml of toluene at about 80° C. BI was prepared from the reaction of 4NPI and BPA, with MI the by-product thereof. This mixture was prepared to simulate ratios of BI product to MI by-product typically found in bisimide reaction product mixtures. 5.1 ml of 1% NaOH (1.25 moles, or 5 moles NaOH per mole of MI) was then added. The resulting mixture was then stirred vigorously with a magnetic stirrer, with the toluene layers sampled after 30, 120, and 600 sec. The HPLC analysis showed the amounts of MI and BI indicated below. The percentages indicated are percentages by weight of the total mixture.

TABLE 5

| | MI (%) | BI (%) |
|---|---|---|
| 0 sec | 2.0 | 98.0 |
| 30 sec | 1.5 | 98.5 |
| 120 sec | 1.0 | 99.0 |
| 600 sec | 0.2 | 99.8 |

The experiment above was repeated except that 1.0 ml of 5% NaOH (1.25 mmole) was added in place of the 5.1 ml of 1% NaOH. The HPLC analysis showed the amounts of MI and BI below. The percentages indicate percentages by weight of the total mixture.

TABLE 6

| | MI (%) | BI (%) |
|---|---|---|
| 0 sec | 2.0 | 98.0 |
| 15 sec | 0.1 | 99.9 |
| 30 sec | <0.1 | >99.9 |
| 120 sec | <0.1 | >99.9 |

As indicated above, the same amount of NaOH was used, only the concentration was increased. The results using 5% NaOH indicate a much faster removal of MI than when using equal amounts of 1% NaOH. Analysis of the aqueous extract from the sample taken after thirty seconds also showed that less than one percent of the BI had been hydrolyzed in this short period of time, thus indicating that extraction efficiency is enhanced using 5% NaOH without causing destruction of the desired BPA-BI product.

Since certain changes may be made in carrying out the above process without departing from the scope of the invention, it is intended that all matters contained in the above description shall be interpreted as illustrative and not in a limiting sense.

What is claimed:

1. A method for removing by-products from a reaction mixture obtained from the reaction of a substituted phthalimide with an alkali metal salt of a hydroxy aromatic compound in a non-polar organic solvent, under imide-forming conditions, comprising extracting the by-products with an aqueous solution of about 4% to about 6% by weight alkali, wherein the by-products are extracted for a residence time of between 1 second and 4 minutes.

2. A method according to claim 1 wherein the substituted phthalimide is reacted with the alkali metal salt of a hydroxy aromatic compound in toluene.

3. A method according to claim 1 comprising extracting the by-products with an aqueous solution of about 4% to about 6% by weight alkali metal hydroxide.

4. A method according to claim 1 comprising extracting the by-products with an aqueous solution of about 5% by weight alkali metal hydroxide.

5. A method according to claim 1 comprising extracting the by-products with an aqueous solution of about 5% by weight sodium hydroxide.

6. A method according to claim 1 wherein the by-products are selected from the group consisting of a substituted phthalimide, a metal salt of a hydroxy aromatic compound, an aromatic ether monoimide, a nitro salt and a halo salt.

7. A method according to claim 1 wherein the reaction of the substituted phthalimide and the alkali metal salt of the hydroxy aromatic compound is carried out in a non-polar organic solvent containing a phase transfer catalyst.

8. A method according to claim 7 wherein the reaction of the substituted phthalimide and the alkali metal salt of the hydroxy aromatic compound is carried out in a non-polar organic solvent containing a bis-tetralkylammonium bromide phase transfer catalyst.

9. A continuous method of preparing an aromatic ether bisimide, the method comprising:
(a) providing at least one substituted phthalimide and at least one alkali metal salt of a hydroxy aromatic compound,
(b) reacting the substituted phthalimide with the alkali metal salt of the hydroxy aromatic compound in a non-polar organic solvent, thereby providing an aromatic ether bisimide and by-products thereof, and
(c) extracting the by-products of the reaction in (b) with an aqueous solution of about 4% to about 6% by weight alkali, wherein the by-products are extracted for a residence time of between 1 second and 4 minutes.

10. A method according to claim 9 wherein (b) comprises a reaction in toluene.

11. A method according to claim 9 comprising extracting the alkali by-products with an aqueous solution of about 4% to about 6% alkali metal hydroxide.

12. A method according to claim 9 comprising extracting the by-products with an aqueous solution of about 5% by weight alkali metal hydroxide.

13. A method according to claim 9 comprising extracting the by-products with an aqueous solution about 5% by weight sodium hydroxide.

14. A method according to claim 9 comprising extracting reaction (b) by-products selected from the group consisting of a substituted phthalimide, a metal salt of a hydroxy aromatic compound, an aromatic ether monoimide, a nitrite salt and a halo salt.

15. A method according to claim 9 wherein step (b) is carried out in a non-polar organic solvent containing a phase transfer catalyst.

16. A method according to claim 15 where step (b) is carried out in a non-polar organic solvent containing a bis-tetraalkylammonium bromide phase transfer catalyst.

17. A method according to claim 9 comprising extracting the by-products of the reaction in no more than two extraction steps, thereby providing a substantially complete extraction of the by-products.

18. A method according to claim 9 comprising extracting the by-products of the reaction in no more than one extraction step, thereby providing a substantially complete extraction of the by-products.

19. A method according to claim 9 wherein the by-products are completely extracted in 30 seconds to one minute.

20. A method according to claim 1 wherein the by-products are completely extracted in 30 seconds to one minute.

21. A method according to claim 1 wherein said residence time is less than 30 seconds.

22. A method according to claim 9 wherein said residence time is less than 30 seconds.

23. A method according to claim 1 wherein said residence time is between 5 seconds and 30 seconds.

24. A method according to claim 9 wherein said residence time is between 5 seconds and 30 seconds.

25. A method according to claim 1 wherein said extracting is completed in one extraction step.

* * * * *